US00PP25776P3

(12) United States Plant Patent
Schoone

(10) Patent No.: US PP25,776 P3
(45) Date of Patent: Aug. 4, 2015

(54) ***PHALAENOPSIS* ORCHID PLANT NAMED 'LIONS DIVE'**

(50) Latin Name: *Phalaenopsis hybrida*
Varietal Denomination: Lions Dive

(71) Applicant: Floricultura, Heemskerk (NL)

(72) Inventor: René Schoone, Assendelft (NL)

(73) Assignee: Floricultura, Hemmskerk (NL)

( * ) Notice: Subject to any disclaimer, the term of this patent is extended or adjusted under 35 U.S.C. 154(b) by 123 days.

(21) Appl. No.: 13/986,290

(22) Filed: Apr. 19, 2013

(65) Prior Publication Data

US 2013/0291247 P1 Oct. 31, 2013

Related U.S. Application Data

(60) Provisional application No. 61/638,441, filed on Apr. 25, 2012.

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

(56) References Cited

U.S. PATENT DOCUMENTS

PP23,701 P3 * 7/2013 Schoone ..... Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Lions Dive' particularly characterized by flowers which are purple/violet with white edges; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Lions Dive'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Lions Dive'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Lions Dive' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Lions Dive' originated from a cross made by the inventor in 1999 in Strengweg, Heemskerk, The Netherlands. The female or seed parent is the *Phalaenopsis* cultivar designated '(Little Mary×Pico Caroline)', unpatented. The male or pollen parent is the *Phalaenopsis* cultivar designated 'Pico Sweetheart' , unpatented. The new *Phalaenopsis* 'Lions Dive' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Lions Dive', which in combination distinguish this *Phalaenopsis* as a new and distinct cultivar:

1. flowers which are purple/violet with white edges;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Lions Dive', the female parent '(Little Mary×Pico Caroline)' has dark pink colored flowers and the male parent 'Pico Sweetheart' has pink colored flowers, whereas the flowers of 'Lions Dive' are purple/violet with white edges.

Presently, the commercial cultivar to which 'Lions Dive' can be meaningfully compared is 'Palazzio' (Patented, U.S. Plant Pat. No. 25,162). The color of the flowers of 'Lions Dive' is purple/violet, whereas the color of 'Palazzio' is purple. 'Palazzio also has more white on the lateral sepals with purple/violet spots. The spots on the lateral sepals of 'Lions Dive' are red/purple. Also differs the shape of the labellum.

BRIEF DESCRIPTION OF THE PHOTOGRAPHS

The accompanying photographs illustrate the overall appearance of the new *Phalaenopsis* 'Lions Dive' showing the colors as true as is reasonably possible with colored reproductions of this type. Colors in the photographs may differ slightly from the color values cited in the detailed botanical description, which accurately describe the color of 'Lions Dive'.

DETAILED BOTANICAL DESCRIPTION

Figure 1:
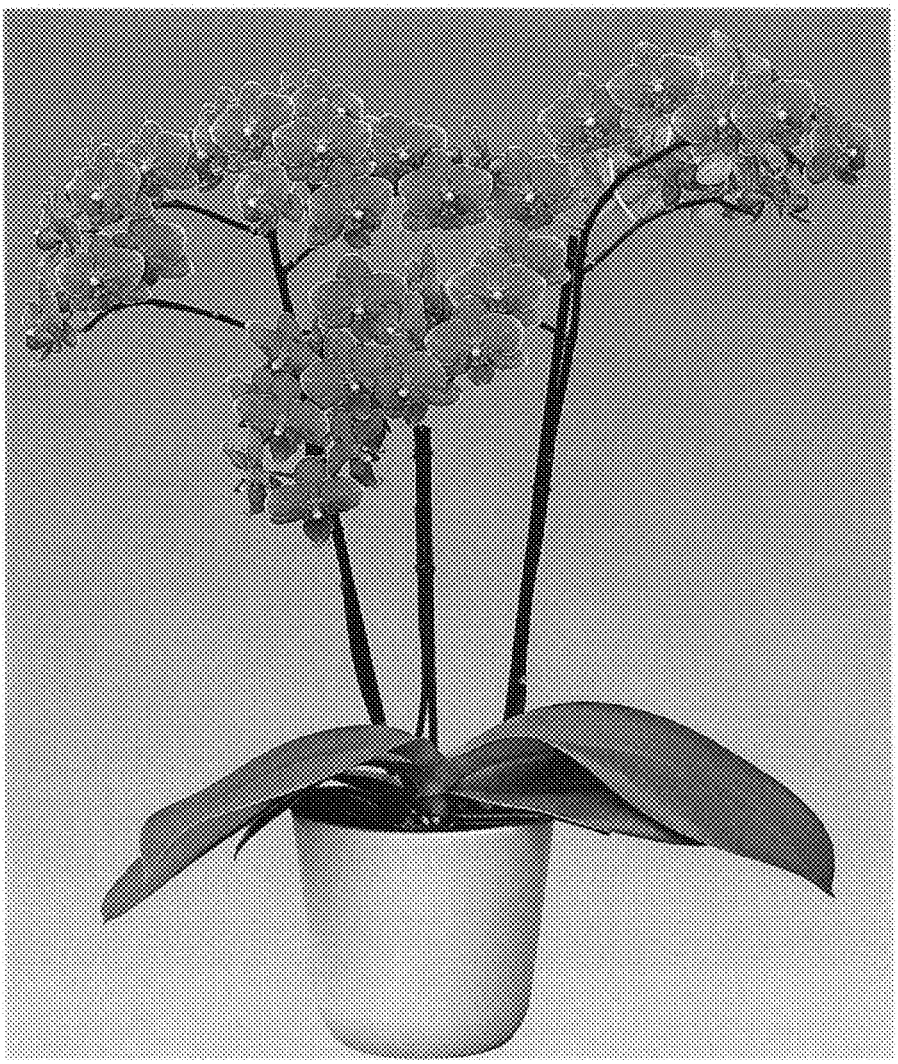
FIG. 1 shows a side view perspective of a typical flowering plant of 'Lions Dive' in a 12 cm pot, at 16 months of age.

The new *Phalaenopsis* cultivar 'Lions Dive' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Lions Dive' as grown in a greenhouse in Strengweg, Heemskerk, The Netherlands, under conditions which closely approximate those generally used in commercial practice. Initially, the ideal temperature to grow plants of 'Lions Dive' is 27° C. during the day and at night. Then, during the flowering phase of 'Lions Dive', the ideal growing temperature is 20-22° C. during the day and 18° C. at night. Light levels for growing 'Lions Dive' are a minimum of 5,000 lux and a maximum of 10,000 lux. A balanced fertilizer with level of 200 ppm N, 87 ppm P, 168 ppm K is applied. Duration of growth of 'Lions Dive' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Lions Dive' plants described is 12 months after potting.

Classification:

*Botanical. —Phalaenopsis hybrida.*

Parentage:

*Female or seed parent.—Phalaenopsis* cultivar designated '(Little Mary×Pico Caroline)', unpatented.

*Male or pollen parent.—Phalaenopsis* cultivar designated 'Pico Sweetheart', unpatented.

Propagation:

*Type.*—Tissue culture.

*Rooting habit and description.*—Fleshy; approximately 4 mm-9 mm wide and green in color (RHS 146B); freely branching. It takes 12 weeks for plants growing in tissue culture to initiate roots.

Plant:

*Size at maturity.*—Height: about 52 cm. Spread: about 45 cm.

*Growth habit.*—Small; dark green leaves (RHS 137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture* (*upper* & *underside*).—Smooth and leathery.

*Pubescence.*—None.

*Mature leaf length.*—About 14 to 20 cm.

*Mature leaf width.*—About 6 to 10 mm.

*Mature leaf thickness.*—About 2 mm.

*Mature leaf color.*—Upper side: green (RHS 137A). Under side: yellow/green (RHS 146B).

*Leaf base.*—Acute.

*Margin.*—Entire.

*Venation.*—Pattern: parallel. Color of midvein: upper side: green (RHS N137A). Under side: yellow/green (RHS 144A).

Inflorescence description:

*Appearance.*—Upright to slightly pendant, racemose inflorescence with bilaterally symmetrical flowers that open in succession beginning with the lowermost flower.

*Buds.*—Height (from base to tip): about 12 mm to 15 mm. Diameter (at midpoint): about 7 mm to 15 mm. Shape: egg-shaped/oval. Color: yellow/green (RHS 144B) and some purple (RHS N79C).

*Raceme.*—Quantity per plant: about 1 to 3. Number of flowers per raceme: about 15 to 30. Length: about 45 to 50 cm.

*Peduncle.*—Diameter: about 3 mm. Strength: strong. Aspect: upright. Texture: glabrous and smooth. Color: yellow/green (RHS 147A) mixed with yellow/green (RHS 144A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
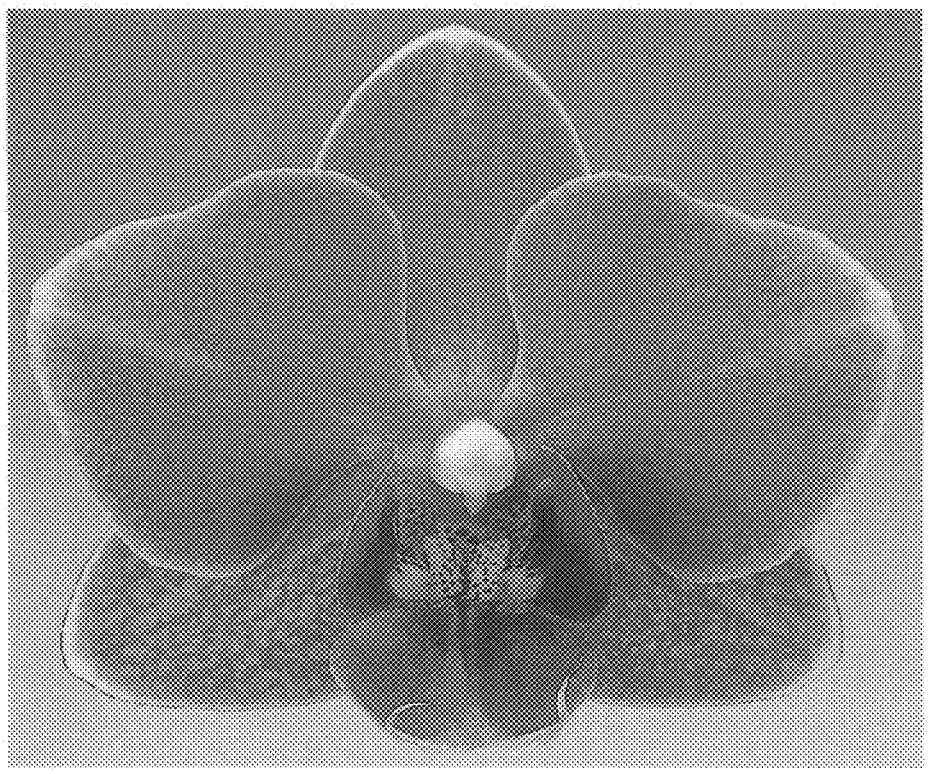
FIG. 2 shows a close-up view of a typical flower of 'Lions Dive'.
Figure 3:
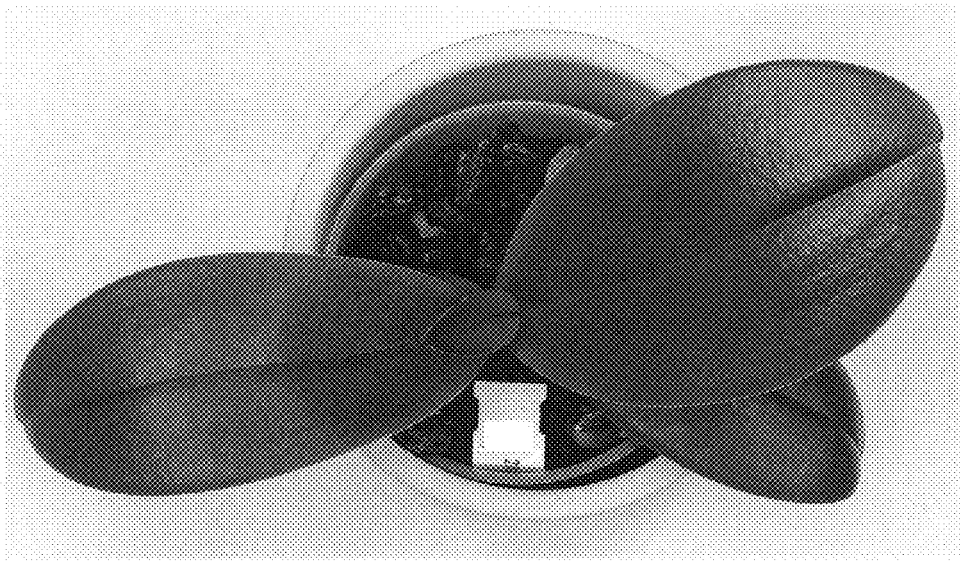
FIG. 3 shows a close-up view of the typical leaves of 'Lions Dive'.

*Flower.*—Rate of opening: Flowers fully opened about 2 to 3 days after petal and sepal separation. Orientation at opening: slanted upward and outward. Shape: typical shape of *Phalaenopsis* orchid; see FIG. 2. Size: Height: about 35 mm to 50 mm. Diameter: about 44 mm to 50 mm. Quantity and arrangement: three petals and three sepals that are trimerous, overlapping and arranged in 2 whorls. Petals are more pronounced than sepals.

*Petals.*—Arrangement: Inner whorl comprises 3 petals: 2 lateral petals and a labellum. 2 lateral petals: Overall shape: little triangular. Apex: oval. Margin: entire and weakly undulate. Base: broadly ovate. Length: about 25 mm. Width: about 23 mm. Texture: Upper surface: smooth and satiny. Under surface: smooth and satiny. Color (when fully opened): upper side: Main color is purple/violet (RHS N81B) with white edges (RHS NN155C). Under side: Main color is purple/violet (RHS N81). Edges are white (RHS NN155C) and in the center a white haze (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is orbicular with a bump and a rib on it. Margin: entire and weakly undulate. Apex: oval. Length midlobe: about 18 mm. Width midlobe (not flattened): about 15 mm. Length lateral lobe: about 14 mm. Width lateral lobe (not flattened): about 8 mm. Depth of tube created by lateral lobes of labellum: about 8 mm. Texture: Upper and under surface: smooth and satiny. Color (when fully opened): Midlobe: upper surface: At the base some grey/orange (RHS 167A) which runs into purple/violet (RHS N80A). From halfway to end white edges (RHS NN155C). Under surface: At the base left and right small edge of grey/orange (RHS 167A), which runs into a haze of purple/violet (RHS N82A). In the center purple (RHS 76C). Lateral lobes: upper surface: At the base white (RHS NN155C) with a yellow spot (RHS 13A). Lower edge is grey/orange (RHS 167A). Close to base small red/purple stripes (RHS 61A). After that an edge of red/purple (RHS 60A), which runs into purple/violet (RHS N80A). Under surface: At the base white (RHS NN155C) which runs into purple (RHS 77A) and after that RHS N80A, with at the lower edge some grey/orange (RHS 167A). Cirrhi: short (about 5 mm). Color: purple/violet (RHS N81C) with white tips (RHS NN155C). Pestle (Callosities): Length: about 4 mm. Width (not flattened): about 4 mm. Color: Sides are white (RHS NN155C). Front, he edges and inside yellow (RHS 13A). Spots are red/purple (RHS 59A).

*Sepals.*—Arrangement: Outer whorl comprises 3 sepals: one dorsal and two lateral sepals. Overall shape: oval and narrow. Margin: entire and weakly undulate. Length: about 24 mm. Width: about 15 mm. Apex: oval/round, little bit pointed. Texture: Upper and under surface: smooth and satiny. Color (when fully opened): upper side: dorsal sepal: purple/violet (RHS N81B) with white edges (RHS NN155C). Lateral sepal: main color is purple/violet (RHS N81B) with white edges (RHS NN155C). At the base a white mark (mixture of RHS N155D and 154D) with red/purples spots (RHS 59A). Under side: dorsal sepals: purple (RHS 74C) with white edges (RHS NN155C). Lateral sepal: main color is purple (RHS 74C) with white edges (RHS NN155C). At the base a small yellow/green mark (RHS 154C).

*Pedicel.*—Length: about 24 to 32 mm. Diameter: about 3 mm. Texture: glabrous and smooth. Color: from yellow/green (RHS 147B) to white (RHS N155B).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 10 mm. Diameter: about 6 mm. Color: Purple/violet (RHS N81C) and white (RHS NN155C).

*Pollinia.*—Quantity: two. Diameter: about 1 mm. Color: orange (RHS 25A).

*Ovary.*—Length: about 3 mm. Diameter: about 4 mm. Color: white (RHS NN155C) and purple edge (RHS N81C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Lions Dive', as illustrated and described herein.

* * * * *